(12) United States Patent
Spallek et al.

(10) Patent No.: US 11,369,708 B2
(45) Date of Patent: Jun. 28, 2022

(54) METHOD FOR REDUCING MICROBIOLOGICAL CONTAMINATION

(71) Applicant: KOCHER-PLASTIK MASCHINENBAU GMBH, Sulzbach-Laufen (DE)

(72) Inventors: Michael Spallek, Ingelheim (DE); Johannes Geser, Gerlingen (DE)

(73) Assignee: KOCHER-PLASTIK MASCHINENBAU GMBH, Sulzbach-Laufen (DE)

(*) Notice: Subject to any disclaimer, the term of this patent is extended or adjusted under 35 U.S.C. 154(b) by 67 days.

(21) Appl. No.: 16/772,904

(22) PCT Filed: Dec. 17, 2018

(86) PCT No.: PCT/EP2018/085235
§ 371 (c)(1),
(2) Date: Jun. 15, 2020

(87) PCT Pub. No.: WO2019/129524
PCT Pub. Date: Jul. 4, 2019

(65) Prior Publication Data
US 2021/0162086 A1    Jun. 3, 2021

(30) Foreign Application Priority Data
Dec. 27, 2017  (DE) ............ 10 2017 012 091.9

(51) Int. Cl.
*A61L 2/20* (2006.01)
*A61L 2/18* (2006.01)
(Continued)

(52) U.S. Cl.
CPC ............... *A61L 2/208* (2013.01); *A61L 2/183* (2013.01); *A61L 2/186* (2013.01); *A61L 2/20* (2013.01);
(Continued)

(58) Field of Classification Search
CPC . A61L 2/18; A61L 2/183; A61L 2/186; A61L 2/20; A61L 2/202; A61L 2/208; A61L 2202/182; A61L 2202/23
See application file for complete search history.

(56) References Cited

U.S. PATENT DOCUMENTS 6,039,921 A    3/2000  Boucher
6,355,216 B1 *  3/2002  Kristiansson ........... A61L 2/087
                                                    422/22
(Continued)

FOREIGN PATENT DOCUMENTS

DE          198 12 057     9/1999
DE       10 2013 012 809   2/2015
(Continued)

OTHER PUBLICATIONS

International Search Report (ISR) dated Oct. 24, 2019 in International (PCT) Application No. PCT/EP2018/085235.

*Primary Examiner* — Timothy C Cleveland
(74) *Attorney, Agent, or Firm* — Wenderoth, Lind & Ponack, L.L.P.

(57) ABSTRACT

A method reduces microbiological contamination in a closed chamber (6), formed by at least two interconnected components (1, 4), by introducing a germicidal medium in liquid form into the chamber (6). The chamber (6) is formed by and between a cap (4) and a head (2) of a filled container.

25 Claims, 2 Drawing Sheets

(51) Int. Cl.
  *B65D 51/00* (2006.01)
  *A61L 101/34* (2006.01)
  *A61L 101/02* (2006.01)
  *A61L 101/06* (2006.01)

(52) U.S. Cl.
  CPC ............ *A61L 2/202* (2013.01); *B65D 51/002* (2013.01); *A61L 2101/02* (2020.08); *A61L 2101/06* (2020.08); *A61L 2101/34* (2020.08); *A61L 2202/182* (2013.01); *A61L 2202/23* (2013.01)

(56) References Cited

U.S. PATENT DOCUMENTS

| | | | |
|---|---|---|---|
| 6,815,206 B2 * | 11/2004 | Lin | .......................... A61L 2/26 436/1 |
| 2006/0231519 A1 | 10/2006 | Py et al. | |
| 2011/0052768 A1 | 3/2011 | Py et al. | |
| 2012/0186697 A1 | 7/2012 | Py et al. | |
| 2014/0014465 A1 | 1/2014 | Schoenberger et al. | |
| 2014/0020331 A1 | 1/2014 | Chin et al. | |
| 2016/0090205 A1 | 3/2016 | Py et al. | |
| 2017/0144790 A1 * | 5/2017 | Spallek | .................. B65D 17/12 |

FOREIGN PATENT DOCUMENTS

| | | |
|---|---|---|
| DE | 10 2017 000 048 | 7/2018 |
| EP | 0 799 621 | 10/1997 |
| EP | 0 858 975 | 8/1998 |
| EP | 2 248 650 | 11/2010 |
| EP | 2 684 673 | 1/2014 |
| WO | 2007/117228 | 10/2007 |
| WO | 2009/095488 | 8/2009 |

* cited by examiner

METHOD FOR REDUCING MICROBIOLOGICAL CONTAMINATION

FIELD OF THE INVENTION

The invention relates to a method for reducing microbiological contamination in a closed chamber formed by at least two interconnected components.

BACKGROUND OF THE INVENTION

In the context of this invention, "microbiological contaminants", or "germs" for short, shall denote contaminants that are also called bioburden in English and that include bacteria, spores, yeasts, fungi, viruses, etc. In the manufacture of containers, in particular of plastic containers, for food, for cosmetics or for medical purposes, in particular for parenterals, or for parenteral nutrition, the microbiological quality of the container or of chambers of the container system prior to their filling and/or use is of fundamental importance. For this purpose, the microbiological contamination has to be reduced. As described in DE 198 12 057 A1, state of the art manufacturing of empty, sealed containers for pharmaceutical purposes uses autoclaving or radiation sterilization to achieve sterility of the empty container interior. To prevent the formation of ozone during radiation sterilization, the container has to be filled with an inert gas such as nitrogen or argon. This process requires container materials that are stable to radiation or sufficiently temperature-stable for autoclaving. Even glass has to be chemically stabilized for this process by adding cerium oxide (EP 0858975 A1). This process is not suitable for container systems in which at least one part of the system already contains a sensitive active substance and its other part is not filled. Such container systems include, for instance, multi-chamber containers such as double-chamber syringes or infusion bottles to which a cap has been attached. Such containers, which are manufactured using the well-known BFS (Blow-Fill-Seal) process, are described in detail in the standard DIN ISO 15759.

For these container systems, the closed, empty, complexly shaped interstice (here briefly referred to as the "chamber") between the head of a filled infusion bottle and its cap has to be safely sterilized, without adversely affecting the temperature-sensitive filling product, for instance solutions of amino acids, inside the bottle. In such cases, the usual terminal sterilization, which is usually performed by autoclaving at temperatures above 100° C. for standard infusion solutions, such as 0.9% saline solution, is not feasible. Radiation sterilization of the empty chamber using electron beams or gamma radiation would require very complex and expensive shielding measures of the filled container part to prevent damage to the filling product owing to irradiation. The commonly used container materials, such as low-density polyethylene or polypropylene, which have only a low temperature stability, preclude any heat treatment of the empty chamber for the significant reduction of the germ count by heat, e.g. by infrared radiation, laser radiation or similar. Due to the complex geometry of the closed chamber and the resulting dead spot effects, direct irradiation using light or light pulses is generally unsuitable to safely reach all surfaces for reducing the germ count.

SUMMARY OF THE INVENTION

With regard to this problem, the invention addresses the problem of specifying a simple and rapid method for significantly reducing the number of microbiological contaminants on the inner surfaces of a microbiologically sealed chamber of complex geometry and small volume, preferably sterilizing this chamber, in particular creating a chamber adjacent to a chamber of the container system filled with a liquid or a solid.

According to the invention, this problem is basically solved by the method providing a "chemical sterilization", in which a germicidal medium is introduced into the chamber. In the simplest case, the germicidal effect in the chamber is produced by the medium introduced before the chamber is closed, without any additional external supply of energy.

An increased germicidal effect can be achieved if the medium inside the chamber is exposed to the effect of an energy source.

With special advantage, a germicidal fluid can be introduced into the chamber as a medium in a metered manner.

Advantageously, the energy source is used to heat the fluid to at least partially transition from the liquid phase to the gaseous phase.

The energy supply can be used to at least partially vaporize the fluid, resulting in a distribution of fluid and fluid vapors inside the chamber to be sterilized.

A particularly rapid evaporation and uniform distribution of fluid and fluid vapors can be achieved if the energy for heating is introduced in the form of radiation pulses.

Preferably, the energy is supplied and the fluid is selected such that the fluid is at least partially chemically modified or degraded during its residence time in the chamber.

The fluid can be held in the chamber for a residence time, during which the concentration of the fluid or its degradation products can be at least partially reduced by permeation out of the chamber. Preferably, the temporal course of the change of the concentration of the fluid and/or its degradation products in the chamber is tracked using spectroscopic methods. Infrared spectroscopy, in particular laser absorption spectroscopy, is preferably used for this purpose.

The evaporation of the fluid by heating it directly, using dielectric heating without any significant heating of the walls delimiting the chamber, is particularly advantageous. To this end, radio waves in the frequency range of 5 MHz to 50 MHz can be used or microwaves can be used for dielectric heating. A frequency range from 500 MHz to 30 GHz can be provided, preferably frequencies of 950 MHz or 2450 MHz or 5800 MHz. Direct dielectric heating of the fluid permits its direct evaporation and immediately subsequent condensation on the colder walls that define the chamber. This process (evaporation, distribution and recondensation) can then be repeated systematically using further radiation pulses.

With particular advantage, an aqueous and/or alcoholic solution containing chlorine, ozone and/or a peroxide, preferably hydrogen peroxide, is provided as the fluid. These solutions can easily be directly heated and evaporated by microwave radiation. During the process, solutions containing ozone or hydrogen peroxide are chemically degraded to the harmless substances of water and oxygen.

Likewise, an antiseptic can be used as a fluid, preferably containing at least one active alcoholic substance, particularly preferably ethanol and/or isopropanol.

The components forming the chamber can be a cap and the head of a container, preferably a container for medical purposes. The components can be formed essentially from at least one plastic, preferably from polyolefins, particularly preferably polypropylene or low-density polyethylene. Radio or microwave radiation does not heat these materials or only very slightly, so that they provide well suited condensation surfaces for fluid vapors.

The respective filled container may advantageously be manufactured using the BFS process. The filled container may have a head membrane having at least one depression. Such containers, which may be manufactured by coextrusion and having multiple layers, may be formed as shown in DE 10 2013 012 809 A1.

Other objects, advantages and salient features of the present invention will become apparent from the following detailed description, which, taken in conjunction with the drawings, discloses preferred embodiments of the present invention.

BRIEF DESCRIPTION OF THE DRAWINGS

Referring to the drawings that form a part of this disclosure.

DETAILED DESCRIPTION OF THE INVENTION

Figure 1:
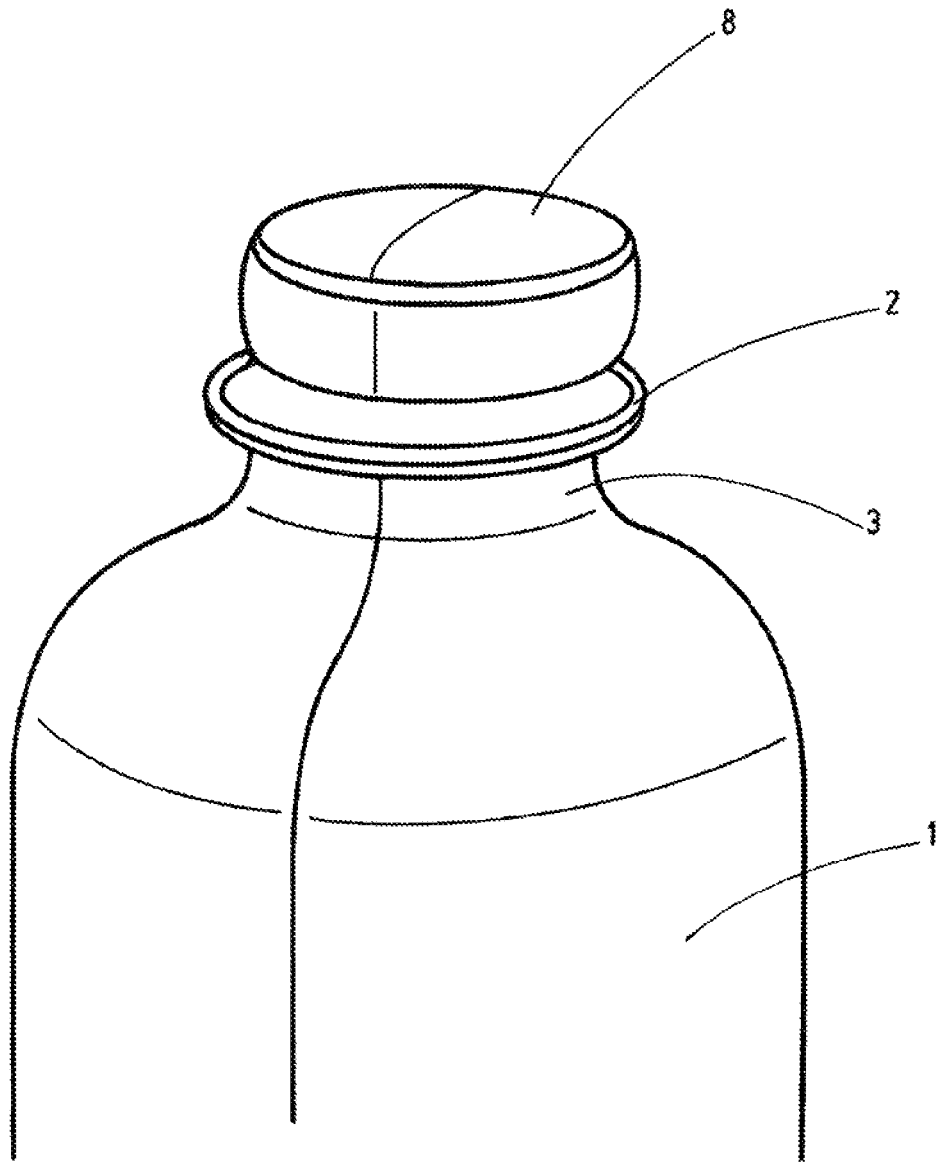
FIG. 1 is a partial perspective view of state-of-the-art infusion container, to the neck collar of which a cap can be attached.

The method of chemical sterilization according to the invention is explained with reference to the attached drawing, using an infusion bottle made of plastic having a tightly attached plastic cap and manufactured according to the BFS process known per se by way of example. An aqueous hydrogen peroxide solution is provided as the germicidal medium. In an analogous way, the invention can also be applied to other container systems mentioned above and using other solvents, germicidal agents, such as known disinfectants (antiseptics), which are also mentioned above. The container 1 shown in FIG. 1 is manufactured and filled according to the BFS process, and has a neck collar 2 at the container neck 3. Above the neck collar 2, a head membrane 8 forms the tight container closure that can be perforated for an infusion process, as described in DIN ISO 15759.

Figure 2:
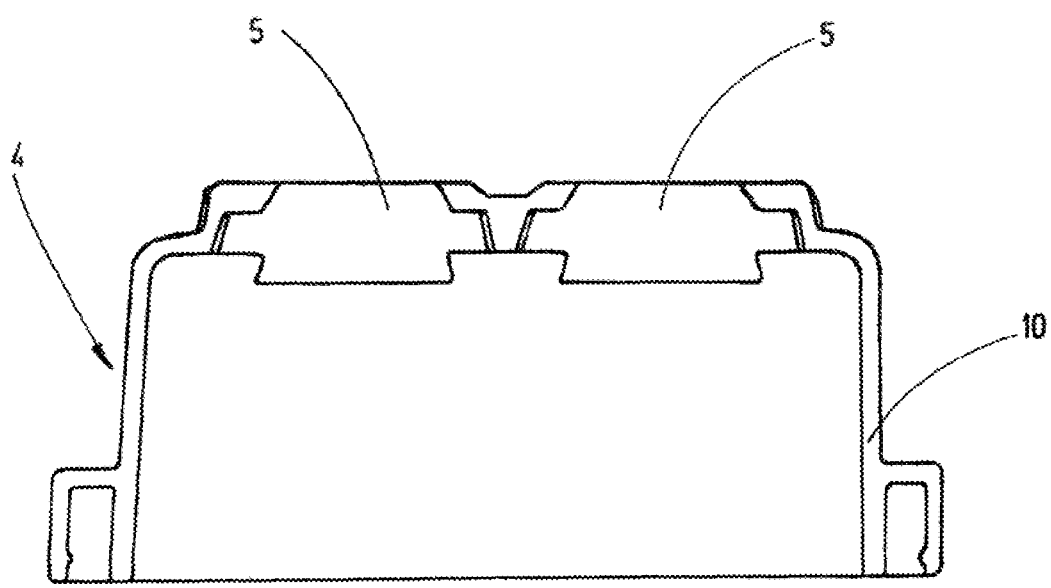
FIG. 2 is a simplified side view in section of a cap that can be attached to the container of FIG. 1.
Figure 3:
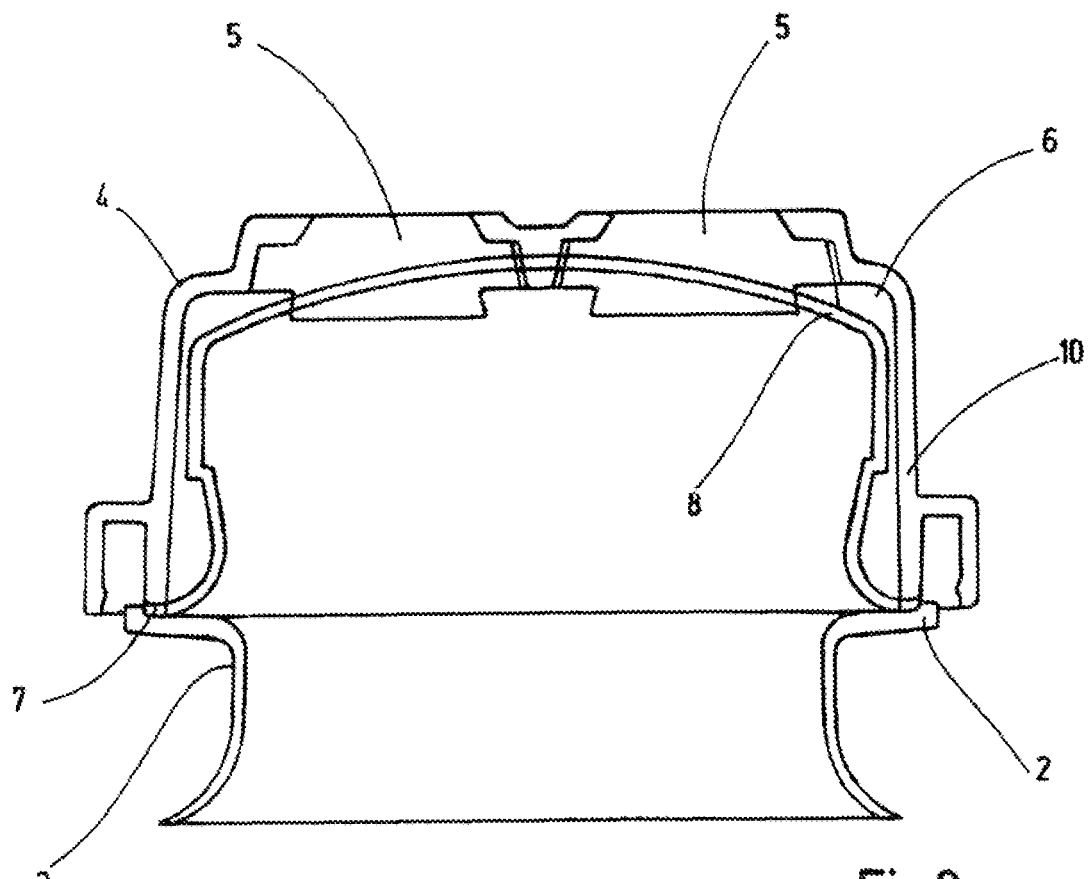
FIG. 3 is in simplified side view in section of the neck collar of the container of FIG. 1 with the cap of FIG. 2 attached.

FIG. 2 shows a cap 4, made of a rigid plastic material and formed according to DIN ISO 15759. As shown in FIG. 3, cap 4 can be tightly welded to the neck collar 2 of the container 1 at the cap edge along a welding point 7, for instance by hot plate welding. The cap 4 could also be tightly connected to the container 1 by over molding. As shown in FIGS. 2 and 3, elastomeric elements 5 sealing the system during use are located at the opening areas of the top of the cap 4 at points that can be pierced by a cannula or spike for an infusion procedure. The elastomeric elements 5 are, as described for instance in the application DE 10 2017 000 048.4, which shows a post-published state of the art made of an elastomer. The elastomer is suitable for being cohesively welded to the material of the cap 4. FIG. 3 shows a chamber 6 closed up in a sealed manner in the cap 4, when the cap 4 is connected to the neck collar 2. The chamber 6 extends along the inside of the circular cylindrical side wall 10 of the cap 4 and along the head membrane 8 and forms an interstice of relatively small volume, which is chemically sterilized by the method according to the invention.

For this purpose, in the example of the method to be described here, a small volume (approx. 0.01 ml to 0.3 ml) of an aqueous hydrogen peroxide solution is metered onto the head membrane 8, for instance by dropping or spraying. Then the cap 8 is sealingly connected to the neck collar 2 so that the chamber 6 is closed in a sealed manner. Alternatively, the fluid can also be sprayed onto the inner surfaces of the cap 4. Direct heating of the applied fluid is achieved by microwave radiation. This microwave radiation has the advantage of heating the fluid directly, while the walls of chamber 6 are warmed only slightly, if at all, such that the radiation itself contributes only indirectly to the reduction of the germ count. At a preferred frequency of microwave radiation in a frequency range of 500 MHz to 30 GHz, the fluid is at least partially evaporated and distributed homogeneously inside the chamber 6. Due to the increase in volume during evaporation, this evaporation results in an overpressure in chamber 6 and thus to the pressure-induced overheating of the hydrogen peroxide. On the one hand, this evaporation initiates the chemical decomposition of the hydrogen peroxide into the harmless substances of water and oxygen. On the other hand, even surfaces that are difficult to access, such as undercuts, gaps, channels and the like, are reliably reached.

Advantageously, microwave pulses are used, which result in a pulsating continuous, at least partial evaporation and repeated micro-condensation of the hydrogen peroxide. A preferred type of condensation, in which extremely small droplets, not visible to the naked eye, are generated. The thermal break-down of the hydrogen peroxide to water and oxygen also sets in. In contrast thereto, in the known methods of sterilizing insulators using gaseous hydrogen peroxide, care must be taken to prevent break-down from occurring in the vaporizer.

An advantage of the method according to the invention is also that no carrier gas is required to transport the gaseous hydrogen peroxide. Gaseous hydrogen peroxide is generated directly in the chamber 6 to be sterilized and at least partially degrading it there. Even sensitive filling products present in the container 1 are not measurably affected. The hydrogen peroxide is already broken-down to a large extent before there is any noticeable permeation into the filling product. Due to the low adsorption and permeation of hydrogen peroxide to and into polyolefins, especially to low-density polyethylenes, such container materials are preferable. As described in DE 103 47 908 A1 for instance, multilayer containers can also be used, whose barrier layers—for example made of ethylene vinyl alcohol copolymer (EVOH) or cycloolefinic components such as cycloolefin copolymers COC (trade name Topas) or cycloolefin polymers COP (trade name Zeonor)—minimize the permeation of the germicidal active substances of the fluid, especially oxygen or alcohols, into the interior of container 1 but not through the cap 4. It is also advantageous to use container headpieces having depressions in the head membrane, as shown in detail in DE 10 2013 012 809 A1.

An advantage of the procedure according to the invention is the very simple gravimetric or volumetric metering of the fluid via the liquid phase. Also, the sterilization conditions can be easily adapted to the volume of the chamber 6, to the geometry of the container system and to its germ load via the quantity and concentration of the hydrogen peroxide solution (typically 3%-35%) introduced into the chamber 6, and can be controlled via the duration, the intensity and the pulse shape of the microwave. A higher reduction in the number of germs can be achieved by several short-term microwave irradiation cycles than by a few, longer-lasting ones. Furthermore, increased hydrogen peroxide concentrations in the gas phase result advantageously in a reduction in the number of germs. The use of ethanolic-aqueous hydrogen peroxide solutions improves the wetting of the surfaces to be sterilized, and thus, also increases the germination reduction.

Experiments to prove the germ count reduction were performed by bio-indicators using spores of *Geobacillus stearothermophilus*. 0.02-0.2 ml of 35% aqueous $H_2O_2$ solutions were metered onto the head membranes 8 of filled 250-ml-infusion bottles made of LDPE. The head membranes had different diameters (20-30 mm). An HDPE cap 4 was welded on the head membranes 8. The volume of the chambers 6 formed in that way was in the range of approximately 1 ml to approximately 3 ml on average. Sterilization experiments were performed using a microwave chamber having an adjustable microwave power of 0.6 KW to 6 KW and an MW transmission frequency of 2450 MHz. The direction of irradiation was parallel to the head membrane 8, i.e. perpendicular to the longitudinal axis of vessel 1. The filled area of vessel 1 was additionally shielded using a close-meshed wire net.

Surprisingly, a significant reduction in the germ count was achieved even in narrow gaps of only a few millimeters wide, in particular between the head membrane 8 and the cap 4 and between the vessel head and the cylindrical part 10 of the cap 4. This effect was all the more successful the more frequently microcondensation occurred, i.e. for an increasing number of irradiation cycles and the resulting pressure pulses.

Moreover, the method in accordance with the invention permits a simple and direct verification of the leak-free application of the infusion cap 4, for instance verification by spectroscopic methods. For this purpose, the content of hydrogen peroxide in the gaseous phase and/or the oxygen content in the chamber 6 can be determined in a non-destructive manner. Laser absorption spectrometers having typical wavelengths in the infrared range between 760 nm and 2000 nm are suitable for this purpose. Alternatively, the concentration of gaseous hydrogen peroxide can be monitored and measured using photo fragmentation laser-induced fluorescence (PF-LIF).

Typically, low power levels are sufficient to generate the microwave pulses, preferably at frequencies of 896 MHz/ 915 MHz/922 MHz (L band) or 2450 MHz (S band) or 5.8 GHz (C band). When using radio waves (frequency range 5 MHz-50 MHz), more power is required due to the weaker coupling, but there is less interference, which significantly reduces hot spots, which cannot always be avoided when using microwaves.

While various embodiments have been chosen to illustrate the invention, it will be understood by those skilled in the art that various changes and modifications can be made therein without departing from the scope of the invention as defined in the claims.

The invention claimed is:

1. A method for reducing microbiological contamination in a closed chamber in a container, comprising the steps of:
   providing a container having a container body filled with contents, a cap and a head of the container body, the cap and the head forming the closed chamber between the cap and the contents; and
   providing a germicidal medium in the closed chamber, the germicidal medium being a liquid when provided into the closed chamber.

2. A method according to claim 1 wherein
   the germicidal medium in the chamber is exposed to an energy source.

3. A method according to claim 1 wherein
   the liquid at least partially transitions into a gaseous phase from the liquid.

4. The method according to claim 3 wherein
   the liquid transitions into the gaseous phase due to heating by an energy source.

5. A method for reducing microbiological contamination in a closed chamber in a container, comprising the steps of:
   providing a container having a container body filled with contents, a cap and a head of the container body, the cap and the head forming the closed chamber between the cap and the contents;
   providing a germicidal medium in the closed chamber, the germicidal medium being a liquid when provided into the closed chamber; and
   the liquid is at least partially vaporized and then condensed at least once in the closed chamber.

6. A method according to claim 5 wherein
   the liquid is at least partially vaporized and then recondensed in the chamber multiple times.

7. A method according to claim 6 wherein
   the liquid is at least partially vaporized by heating from radiation pulses.

8. A method according to claim 5 wherein
   the liquid is at least partially vaporized by exposure to radiation.

9. A method according to claim 8 wherein
   the radiation only heats the liquid without heating the container.

10. A method according to claim 1 wherein
    the liquid is at least one of partially chemically modified or degraded during a residence time of the liquid in the chamber.

11. A method according to claim 10 wherein
    at least one of the concentration of the liquid or degradation products of the liquid are at least partially reduced by permeation out of the chamber during the residence time.

12. A method according to claim 11 wherein
    changes in the concentration and degradation products in the chamber is tracked using a non-destructive spectroscopic method.

13. A method according to claim 8 wherein
    the radiation dielectrically heats the liquid using radio waves in a frequency range of 5 MHz to 50 MHz.

14. A method according to claim 8 wherein
    the radiation dielectrically heats the liquid using microwaves in a frequency range of 500 MHz to 30 GHz.

15. A method according to claim 14 wherein
    the microwaves have a frequency of 915 MHz or 2450 MHz or 5800 MHz.

16. A method according to claim 1 wherein
    the liquid comprises a solution containing at least one of chlorine, ozone or a peroxide.

17. A method according to claim 1 wherein
    the liquid contains hydrogen peroxide.

18. A method according to claim 1 wherein
    the liquid comprises a solution containing at least one of water or alcohol.

19. A method according to claim 1 wherein
    the liquid comprises a solution containing water and ethanol.

20. A method according to claim 1 wherein
    the liquid contains an antiseptic.

21. A method according to claim 1 wherein
    the liquid contains at least one of ethanol or isopropanol.

22. A method according to claim 1 wherein the head and the cap are essentially formed of plastic being at least one of polypropylene or polyethylene.

23. A method according to claim 1 wherein the container is produced by a blow molding, filling and sealing method.

24. A method according to claim 1 wherein the container comprises a head membrane.

25. A method according to claim 1 wherein the container has multiple layers of at least one of an ethylene-vinyl alcohol copolymer, a cycloolefin polymer or a cycloolefin copolymer.

* * * * *